(12) United States Patent
Shoji (10) Patent No.: US 7,254,214 B2
(45) Date of Patent: Aug. 7, 2007

(54) X-RAY IMAGING DEVICE

(75) Inventor: Takashi Shoji, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 10/969,052

(22) Filed: Oct. 21, 2004

(65) Prior Publication Data

US 2005/0087694 A1    Apr. 28, 2005

(30) Foreign Application Priority Data

Oct. 24, 2003  (JP) ............................. 2003-364332

(51) Int. Cl.
*H05G 1/64* (2006.01)
(52) U.S. Cl. ................. 378/98.8; 250/370.07
(58) Field of Classification Search ............... 378/98.8, 378/108; 250/370.07, 370.08, 370.09, 370.11
See application file for complete search history.

(56) References Cited

U.S. PATENT DOCUMENTS

| | | | | |
|---|---|---|---|---|
| 5,818,898 | A | 10/1998 | Tsukamoto et al. | 378/98.8 |
| 5,949,848 | A * | 9/1999 | Gilblom | 378/98.8 |
| 6,151,383 | A * | 11/2000 | Xue et al. | 378/108 |
| 6,268,614 | B1 | 7/2001 | Imai | 250/591 |
| 6,442,238 | B2 * | 8/2002 | Meulenbrugge | 378/98.8 |
| 2002/0001366 | A1 * | 1/2002 | Tamura et al. | 378/155 |
| 2005/0111617 | A1 * | 5/2005 | Shoji | 378/37 |

FOREIGN PATENT DOCUMENTS

| | | |
|---|---|---|
| EP | 0 792 065 A2 | 8/1997 |
| EP | 1 035 421 A2 | 9/2000 |
| JP | 58-223145 A | 12/1983 |
| JP | 60-198097 A | 10/1985 |
| JP | 2000-244824 A | 9/2000 |
| JP | 2001-305232 A | 10/2001 |

OTHER PUBLICATIONS

Japanese Abstract No. 2001305232, dated Oct. 31, 2001.
Japanese Abstract No. 60198097, dated Oct. 7, 1985.
Japanese Abstract No. 58223145, dated Dec. 24, 1983.

* cited by examiner

*Primary Examiner*—Courtney Thomas
(74) *Attorney, Agent, or Firm*—Sughrue Mion, PLLC (57) ABSTRACT

An X-ray imaging device is equipped with a solid state detector, for recording image information by being irradiated with X-rays that bear image information and for outputting image signals that represent the recorded image information, and an X-ray dosage detector for detecting the dosage of irradiated X-rays. The X-ray dosage detector is provided between an X-ray source and the solid state detector, thereby enabling accurate measurement of the X-ray dosage, without being influenced by the solid state detector. In addition, the X-ray dosage detector is equipped with a photoconductive layer. Therefore, the X-ray dosage detector can be made thinner than conventional X-ray dosage detectors, which are constituted by a fluorescent plate, a light collecting field, a light transmitting plate, and a light shielding plate. Accordingly, decreases in resolution of images detected by the solid state detector can be prevented.

17 Claims, 8 Drawing Sheets

X-RAY IMAGING DEVICE

BACKGROUND OF THE INVENTION

1. Field of the Invention

The present invention relates to an X-ray imaging device that obtains an X-ray image of a subject, by detecting X-rays that have passed through the subject.

2. Description of the Related Art

Presently, various X-ray imaging apparatuses, for obtaining X-ray images to be utilized for medical diagnoses, have been proposed and are in practical use. These X-ray imaging apparatuses employ solid state detectors (having semiconductors as main components thereof) as X-ray image detecting means. The solid state detectors detect X-rays that have passed through subjects, and obtain image signals that represent X-ray images of the subject.

A variety of formats have been proposed for the solid state detectors to be utilized in these apparatuses. Regarding a charge generating process for converting X-rays to electrical charges, there is a photo conversion type of solid state detector, and a direct conversion type of solid state detector, for example. The photo conversion type of solid state detector temporarily stores signal charges, obtained at a photoconductive layer by detecting fluorescence emitted by phosphors due to irradiation with X-rays, in a charge accumulating portion, then converts the accumulated charges to image signals (electrical signals) and outputs the image signals. The direct conversion type of solid state detector temporarily stores signal charges, generated within a photoconductive layer due to irradiation with X-rays and collected by a charge collecting electrode, in a charge accumulating portion, then converts the accumulated charges to electric signals and outputs the electric signals. In this type of solid state detector, the main components are the photoconductive layer and the charge collecting electrode.

Regarding a charge readout process for reading out the accumulated charges, there are an optical readout technique and a TFT readout technique. In the optical readout technique, accumulated charges are read out by irradiating a solid state detector with readout light (electromagnetic waves for readout). In the TFT readout technique, accumulated charges are read out by scanning TFT's (thin film transistors), which are connected to a charge accumulating portion. The TFT readout technique is disclosed in Japanese Unexamined Patent Publication No. 2000-244824.

An improved direct conversion type solid state detector has also been proposed in U.S. Pat. No. 6,268,614. The improved direct conversion type solid state detector is a direct conversion type of solid state detector that utilizes the optical readout technique. This solid state detector comprises: a recording photoconductive layer that exhibits photoconductivity when irradiated by recording light (X-rays, or fluorescence generated by the irradiation of X-rays); a charge transport layer that acts substantially as an insulator with respect to charges having the same polarity as latent image charges, and that acts substantially as a conductor with respect to charges having the opposite polarity as latent image charges; and a readout photoconductive layer that exhibits photoconductivity when irradiated by electromagnetic waves for readout; stacked in this order. Signal charges (latent image charges) that bear image information are accumulated at an interface (charge accumulating portion) between the recording photoconductive layer and the charge transport layer. Electrodes (a first conductive layer and a second conductive layer) are provided on both sides of the three aforementioned layers. In the solid state detector having this format, the recording photoconductive layer, the charge transport layer, and the readout photoconductive layer are the main components.

In medical X-ray imaging, there are apparatuses other than those that employ the aforementioned solid state detectors. Examples of alternative X-ray image detecting means are imaging plates and film. However, in all cases, it is necessary to control the dosage of X-rays irradiated onto the X-ray image detecting means during X-ray imaging, to obtain optimal images. Therefore, apparatuses that detect the X-ray dosage irradiated on X-ray image detecting means, and apply the detected X-ray dosage to control the irradiated X-ray dosage are disclosed in Japanese Unexamined Patent Publication Nos. 2001-305232, 58(1983)-223145, and 60(1985)-198097.

In the X-ray imaging apparatus disclosed in Japanese Unexamined Patent Publication No. 2001-305232, a solid state detector is employed as the X-ray image detecting means, and an X-ray dosage detector that detects X-ray dosages is provided on the rear surface of the solid state detector. However, if the X-ray dosage detector is provided on the rear side of the solid state detector, the accuracy in detection of the X-ray dosage is low. This is due to the fact that a large portion of X-rays is absorbed by the solid state detector. In addition, the X-rays irradiated by a radiation source possess a wide energy spectrum. However, low energy components are largely absorbed by the solid state detector, thereby changing the spectrum balance of the X-rays detected by the X-ray dosage detector.

In the apparatus disclosed in Japanese Unexamined Patent Publication No. 58(1983)-223145, an imaging plate is employed as the X-ray image detecting means, and an X-ray dosage detector is provided on the front surface of the imaging plate. However, there is no description regarding what manner of X-ray dosage detector is employed.

In the apparatus disclosed in Japanese Unexamined Patent Publication No. 60(1985)-198097, film is employed as the X-ray image detecting means, and an X-ray dosage detector is provided on the front surface of a film cassette that houses the film therein. However, the X-ray dosage detector is constituted by a fluorescent plate, a light collecting field, a light transmitting plate, and a light shielding plate, causing the structure to be complex, and limiting the degree to which the detector can be made thin. Therefore, the distance between a subject and the film for detecting an X-ray image of the subject cannot be made short, thereby decreasing the resolution of the X-ray image.

That is, no X-ray imaging apparatus has been disclosed to date that employs a solid state detector as the X-ray image detecting means and accurately detects the dosage of irradiated X-rays, to be applied toward controlling the irradiated dosage of X-rays, without adversely affecting detection of an image by the solid state detector.

SUMMARY OF THE INVENTION

The present invention has been developed in view of the above circumstances. It is an object of the present invention to provide an X-ray imaging device that employs a solid state detector as an X-ray image detecting means, and improves the accuracy in detecting X-ray dosages, to be applied toward controlling irradiated dosages of X-rays, without adversely affecting detection of an image by the solid state detector.

The X-ray imaging device according to the present invention comprises:

a solid state detector for receiving irradiation of X-rays that bear image information to record the image information, and for outputting image signals that represent the recorded image information; and an X-ray dosage detector, which is provided between a radiation source of the X-rays and the solid state detector, for detecting the dosage of the irradiated X-rays; wherein the X-ray dosage detector is equipped with a photoconductive layer that exhibits photoconductivity when irradiated by X-rays.

In the present invention, the "solid state detector" refers to a detector that detects X-rays that bear image information of a subject, and outputs image signals that represent an X-ray image of the subject. The solid state detector converts the X-rays irradiated thereon to electrical charges either directly or after converting the X-rays to light, and outputs the charges to the exterior thereof. Thereby, image signals that represent an X-ray image of the subject are obtained.

There are a variety of formats for the solid state detector. Regarding a charge generating process for converting X-rays to electrical charges, there is a photo conversion type of solid state detector, and a direct conversion type of solid state detector, for example. The photo conversion type of solid state detector temporarily stores signal charges, obtained at a photoconductive layer by detecting fluorescence emitted by phosphors due to irradiation with X-rays, in a charge accumulating portion, then converts the accumulated charges to image signals (electrical signals) and outputs the image signals. The direct conversion type of solid state detector temporarily stores signal charges, generated within a photoconductive layer due to irradiation with radiation and collected by a charge collecting electrode, in a charge accumulating portion, then converts the accumulated charges to electric signals and outputs the electric signals. Regarding a charge readout process for reading out the accumulated charges, there are an optical readout technique and a TFT readout technique. In the optical readout technique, accumulated charges are read out by irradiating a solid state detector with readout light (electromagnetic waves for readout). In the TFT readout technique, accumulated charges are read out by scanning TFT's (thin film transistors), which are connected to a charge accumulating portion. Further, there are solid state detectors that combine the direct conversion type and the optical readout method, such as the improved direct conversion type solid state detector, as disclosed in U.S. Pat. No. 6,268,614.

In the X-ray imaging device according to the present invention, the X-ray dosage detector may be formed on a substrate, which has one of resin, carbon, and aluminum oxide as its main component. The X-ray dosage detector may also be integrally formed with the solid state detector.

It is preferable that the X-ray dosage detector is capable of detecting X-ray dosages independently for a plurality of different regions of an X-ray incident surface, on which X-rays are incident.

In addition, it is preferable that the X-ray dosage detector has conductive layers on both a front surface and a rear surface of the photoconductive layer; and at least one of the conductive layers is constituted by a plurality of conductive portions, which are formed separately on the surface of the photoconductive layer. Note that "a front surface and a rear surface of the photoconductive layer" refers to the incident surface and the surface opposite thereto, respectively, of the photoconductive layer.

Further, it is preferable that the solid state detector is equipped with a photoconductive layer that exhibits photoconductivity when irradiated by X-rays; and the X-ray absorption spectrum of the photoconductive layer of the solid state detector is substantially equal to the X-ray absorption spectrum of the photoconductive layer of the X-ray dosage detector.

Still further, the X-ray dosage detector and the solid state detector may be housed within a casing, which is the same size as a film cassette.

The X-ray imaging device according to the present invention comprises a solid state detector for receiving irradiation of X-rays that bear image information to record the image information, and for outputting image signals that represent the recorded image information; and an X-ray dosage detector for detecting the dosage of the irradiated X-rays, wherein the X-ray dosage detector is provided between a radiation source of the X-rays and the solid state detector. Therefore, the X-ray dosage can be accurately measured without being affected by the solid state detector. In addition, the X-ray dosage detector comprises a photoconductive layer that exhibits photoconductivity when irradiated with X-rays. Therefore, the X-ray dosage detector of the present invention can be made thinner than conventional X-ray dosage detectors, which are constituted by a fluorescent plate, a light collecting field, a light transmitting plate, and a light shielding plate. Accordingly, decreases in resolution of images detected by the solid state detector can be prevented.

The X-ray dosage detector may be formed on a substrate, which has one of resin, carbon, and aluminum oxide as its main component. Resin, carbon, aluminum oxide substrates have lower absorption factors with respect to X-rays compared to glass substrates. Therefore, adverse effects to detection of X-ray images by the solid state detector are reduced, and the image quality of images detected by the solid state detector can be improved. Further, the X-ray dosage detector and the solid state detector may be formed integrally. In this case, the apparatus can be made thinner. In addition, the necessity of a substrate between the X-ray dosage detector and the solid state detector is obviated, further improving the image quality of images detected by the solid state detector.

The X-ray dosage detector may be configured to be capable of detecting X-ray dosages independently for a plurality of different regions of an X-ray incident surface, on which X-rays are incident. In this case, the X-ray dosage can be detected for each specific portion within an image. Therefore, the control of the dosage of irradiated X-rays can be performed more precisely.

The X-ray dosage detector may have conductive layers on both a front surface and a rear surface of the photoconductive layer; and at least one of the conductive layers may be constituted by a plurality of conductive portions, which are formed separately on the surface of the photoconductive layer. In this case, fabrication of the X-ray dosage detector being capable of detecting X-ray dosages independently for a plurality of different regions of the X-ray incident surface is facilitated.

The solid state detector may be equipped with a photoconductive layer that exhibits photoconductivity when irradiated by X-rays. In this case, the X-ray absorption spectrum of the photoconductive layer of the solid state detector may be made substantially equal to the X-ray absorption spectrum of the photoconductive layer of the X-ray dosage detector. If the above configuration is adopted, adverse effects to the detection of X-ray images by the solid state detector can be reduced, thereby improving the image quality of images detected by the solid state detector.

The X-ray dosage detector and the solid state detector may be housed within a casing the same size as a film cassette. In this case, they may be employed easily within existing apparatuses configured to use film cassettes.

DESCRIPTION OF THE PREFERRED EMBODIMENTS

Figure 1:
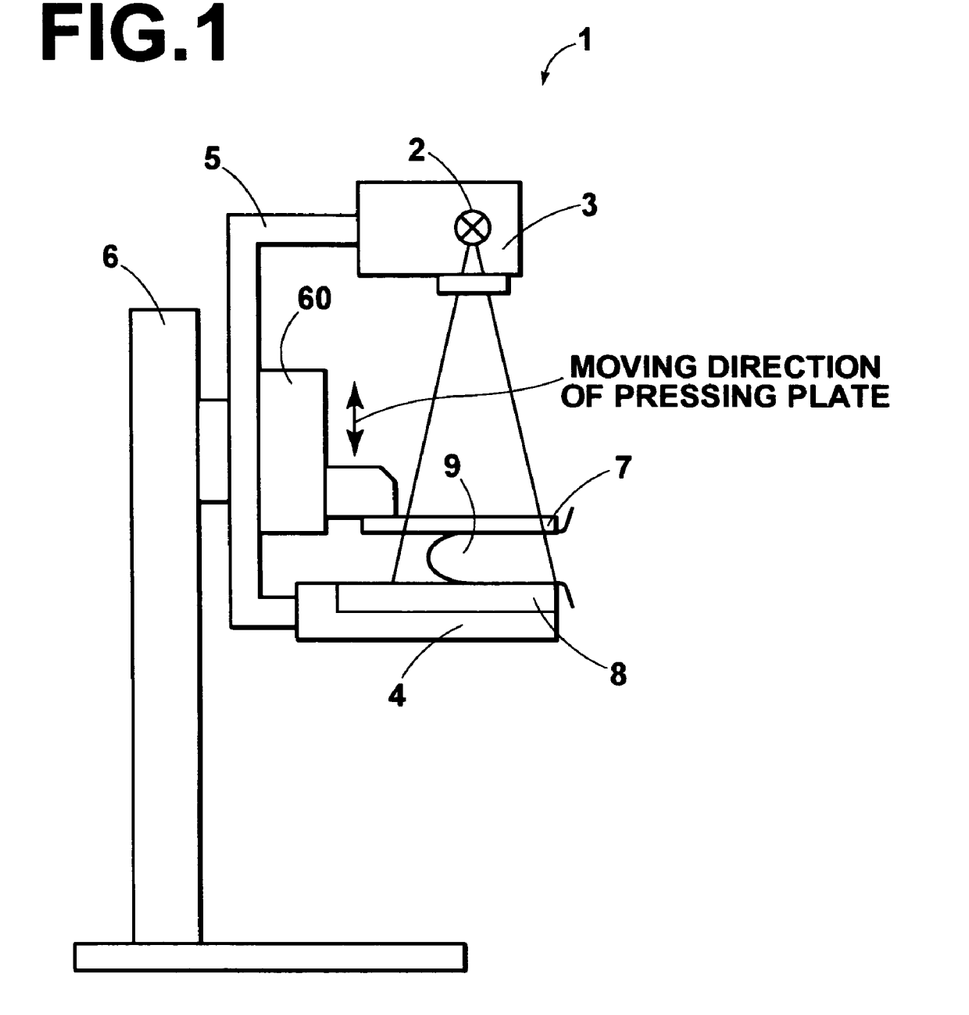
FIG. 1 is a schematic diagram illustrating an example of a mammography apparatus, to which the X-ray imaging device according to the present invention is applied.
Figure 2:
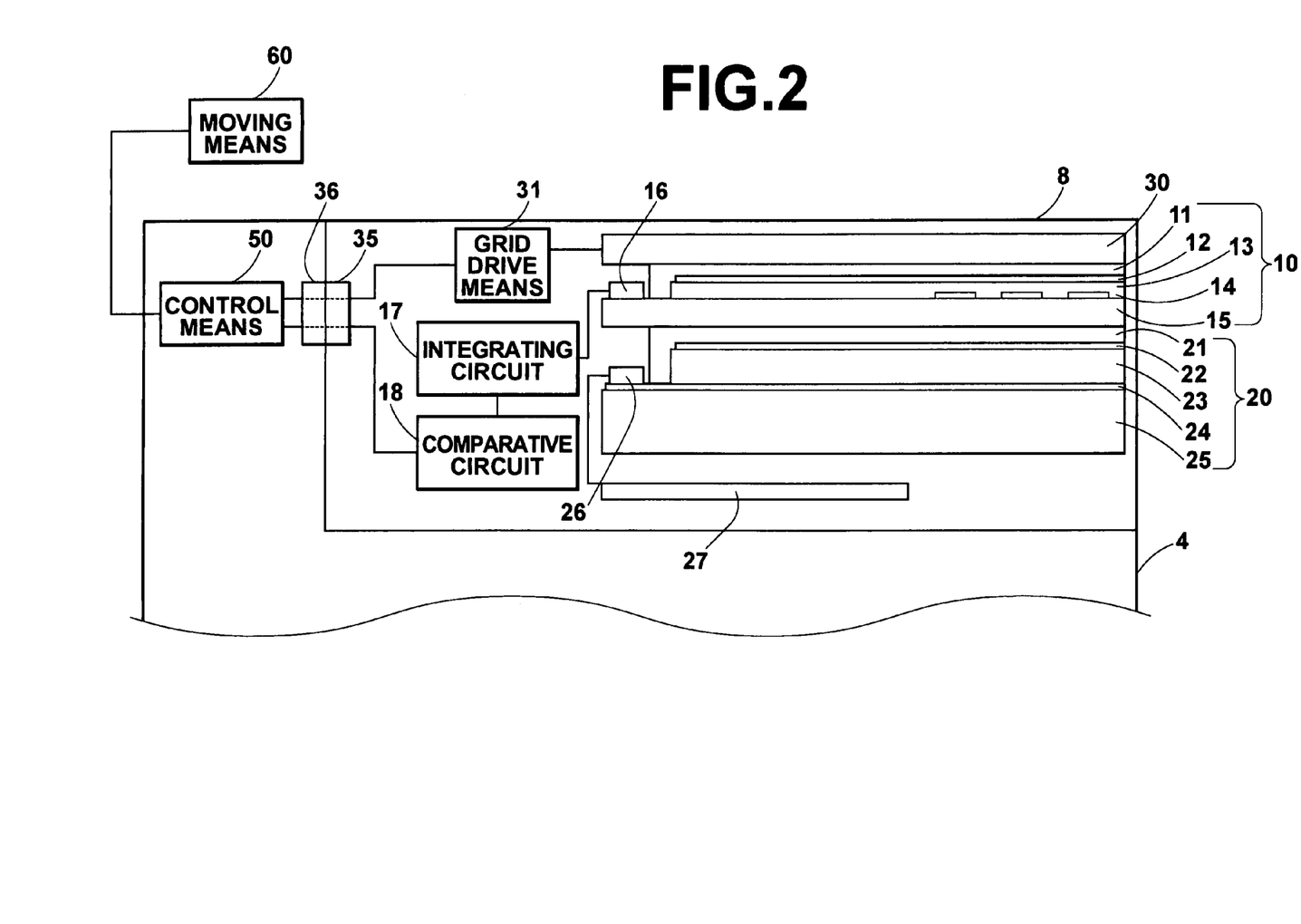
FIG. 2 is a schematic diagram illustrating the interior of a film cassette of the mammography apparatus.
Figure 3:
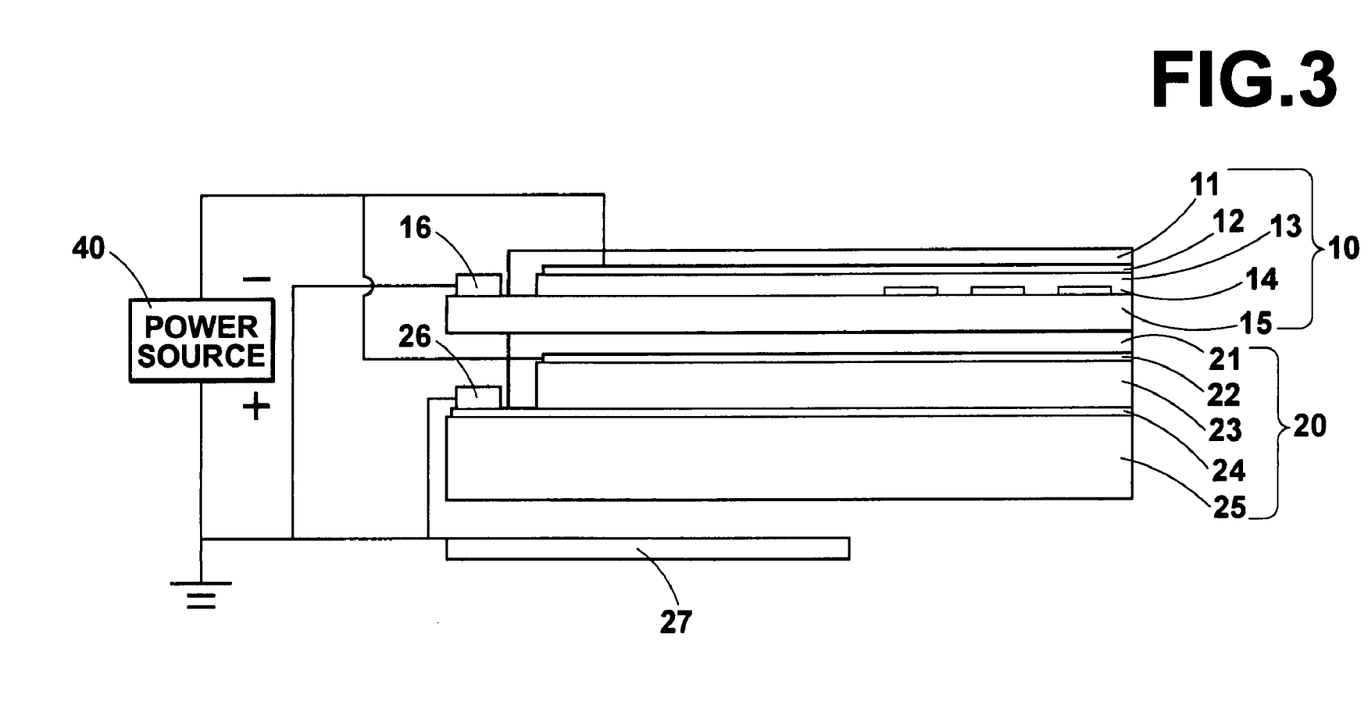
FIG. 3 is a schematic diagram illustrating the manner in which a power source is connected within the film cassette.
Figure 4:
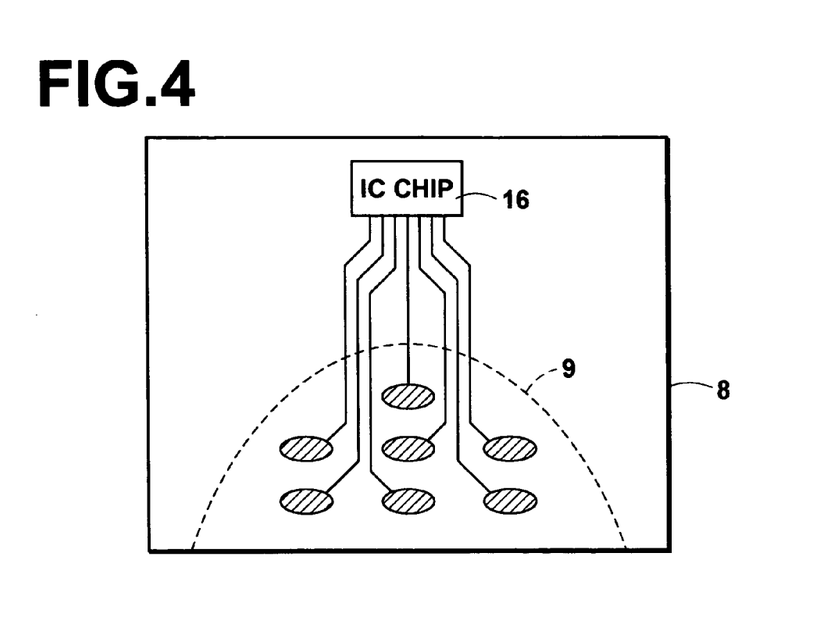
FIG. 4 is a schematic diagram illustrating a conductive layer portion of an X-ray dosage detector of the mammography apparatus.
Figure 5:
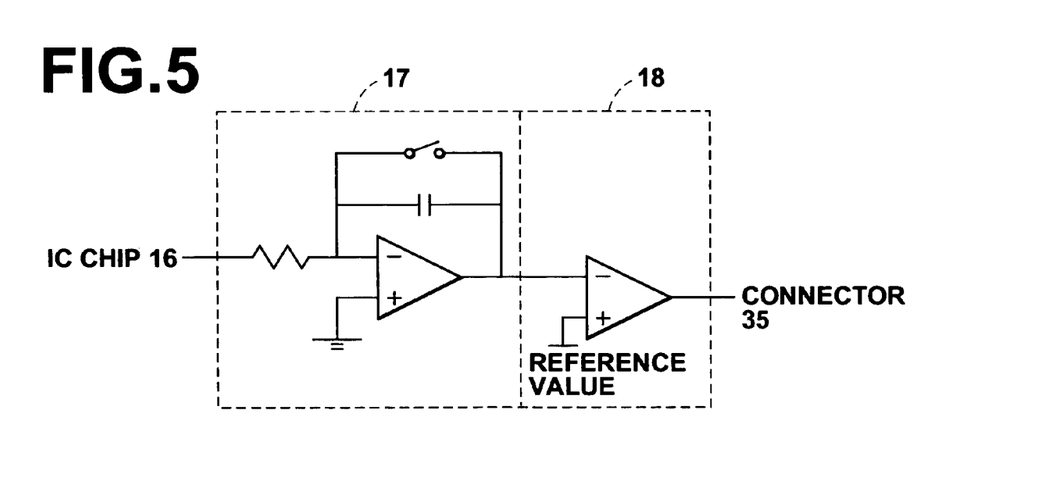
FIG. 5 is a circuit diagram illustrating an integrating circuit and a comparative circuit of the mammography apparatus.

Hereinafter, an embodiment of the present invention will be described in detail with reference to the attached drawings. FIG. 1 is a schematic diagram illustrating an example of a mammography apparatus, to which the X-ray imaging device according to the present invention is applied. FIG. 2 is a schematic diagram illustrating the interior of a film cassette of the mammography apparatus. FIG. 3 is a schematic diagram illustrating the manner in which a power source is connected within the film cassette. FIG. 4 is a schematic diagram illustrating a conductive layer portion of an X-ray dosage detector of the mammography apparatus. FIG. 5 is a circuit diagram illustrating an integrating circuit and a comparative circuit of the mammography apparatus.

A mammography apparatus 1 comprises: an X-ray source housing portion 3 that houses an X-ray source 2 within its interior; an imaging table 4 for holding a film cassette 8, which is an X-ray imaging device; arms 5; and a base 6. The X-ray source housing portion 3 and the imaging table 4 are linked by the arms 5 so that they face each other. The arms are mounted on the base 6.

Further, a pressing plate 7, for pressing and holding a subject's breast 9 from above, and a pressing plate moving means 60, for moving the pressing plate 7 automatically in response to commands from a control means 50, are mounted on the arms 5. The pressing plate moving means 60 is constituted by a linear motor (not shown). The pressing plate moving means 60 moves the pressing plate 7 reciprocally between a first position, at which the breast 9 is pressed against the film cassette held on the imaging table 4, and a second position, at which the pressure is released.

An X-ray dosage detector 10, for detecting the dosage of X-rays irradiated on the film cassette 8; a solid state detector 20, which is an imaging device; a moving grid 30, for removing scattered radiation; a grid drive means 31, for driving the moving grid 30; and a power source 40, for supplying electricity to the above components, are provided within the film cassette 8.

The X-ray dosage detector comprises: a first conductive layer 14; a photoconductive layer 13 that generates electrical charges and exhibits conductivity when irradiated with X-rays; a second conductive layer 12; and an insulative layer 11, stacked in this order on a resin substrate 15.

The first conductive layer 14 comprises a plurality of conductive layer portions 14a, which are formed separated from each other, as illustrated in FIG. 4. Each of the conductive layer portions 14a is connected to an IC chip 16. As described above, the plurality of conductive layer portions 14a are formed separated from each other. Thereby, the X-ray dosage of a region of most interest corresponding to the shape of a breast, for example, may be controlled. In the case that a fluorescent plate, a light collecting field, a light transmitting plate, and a light shielding plate are employed, a plurality of these sets must be prepared. This increases the cost and requires the device to be thick. However, according to the present invention, the device can be realized at low cost, and can be formed thin. Further, the IC chip 16 is connected to an integrating circuit 17, and the integrating circuit 17 is connected to a comparative circuit 18.

The X-ray dosage detector 10 operates in the following manner. Electric fields are formed between each of the conductive layer portions 14a of the first conductive layer 14 and the second conductive layer 12. If X-rays are irradiated onto the photoconductive layer 13 at this time, charge pairs are generated within the photoconductive layer 13. Current corresponding to the amount of charge pairs flows between each conductive layer portion 14a and the second conductive layer 12, and the current is converted to voltage by the IC chip 16.

The integrating circuit 17 converts the current that flows between each conductive layer portion 14a and the second conductive layer 12 into voltages, and integrates the converted voltages. In the case that the voltages integrated by the integrating circuit 17 exceed a predetermined value, the comparative circuit 18 outputs data indicating this fact. Thereby, judgment can be made regarding whether the X-ray dosage irradiated on the film cassette 8 has exceeded a predetermined value. Optimal X-ray dosages vary depending on factors such as the thickness of the breast to be imaged, the tube voltage of the X-ray source, the target material of the X-ray source, and the radiation source filter. Therefore, it is preferable that a reference value (predetermined value) to be input to the comparative circuit be varied, according to the imaging conditions described above.

Note that the judgment regarding whether the X-ray dosage irradiated on the film cassette 8 has exceeded the predetermined value may be made based on the current that flows between any one of the plurality of conductive layer portions 14a and the second conductive layer 12, or based on the total current that flows between each of the plurality of conductive layer portions 14a and the second conductive layer 12.

The solid state detector 20 comprises: a first conductive layer 24 formed of a-Si TFT's; a photoconductive layer 23 that exhibits conductivity by generating charges when irradiated with X-rays; a second conductive layer 22; and an insulative layer 21, which are stacked in this order on a glass substrate 25.

A TFT is formed corresponding to each pixel in the first conductive layer 24. Output from each TFT is connected to an IC chip 26, and the IC chip 26 is connected to a printed circuit board 27, which is equipped with an A/D converting portion, a memory, and the like (not shown).

The solid state detector 20 operates in the following manner. An electric field is formed between the first conductive layer 24 and the second conductive layer 22. If X-rays are irradiated onto the photoconductive layer 23 at this time, charge pairs are generated within the photoconductive layer 23. Latent image charges corresponding to the amount of charge pairs are accumulated within the first conductive layer 24. When reading out the accumulated latent image charges, the TFT's of the first conductive layer 24 are sequentially driven to read out the latent image charges corresponding to each pixel. Thereby, an electrostatic latent image borne by the latent image charges are read out.

The aforementioned X-ray dosage detector 10 is stacked on top of the solid state detector 20, and configured to be positioned between the X-ray source 2 and the solid state detector 20 when the film cassette 8 is held on the imaging table 4. For this reason, the X-ray dosage detector 10 is capable of directly detecting the X-rays emitted from the X-ray source, without the solid state detector 20 acting as an intermediary. Therefore, the X-ray dosage can be accurately measured, without being influenced by the solid state detector 20. In addition, because the photoconductive layer 13 that exhibits photoconductivity when irradiated by X-rays is provided, the X-ray dosage detector 10 can be made thinner than conventional X-ray dosage detectors that employ a fluorescent plate, a light collecting field, a light transmitting plate, a light shielding plate, and the like. Therefore, decrease in the resolution of images detected by the solid state detector 20 can be prevented. Further, because the X-ray dosage detector 10 is formed on a resin substrate 15, which has a lower X-ray absorption rate than glass substrates, adverse influences on detection of X-ray images by the solid state detector 20 are reduced. Accordingly, the image quality of images detected by the solid state detector 20 is improved.

As illustrated in FIG. 3, power is supplied to the X-ray dosage detector 10 and the solid state detector 20 from the same power source 40.

Figure 7:
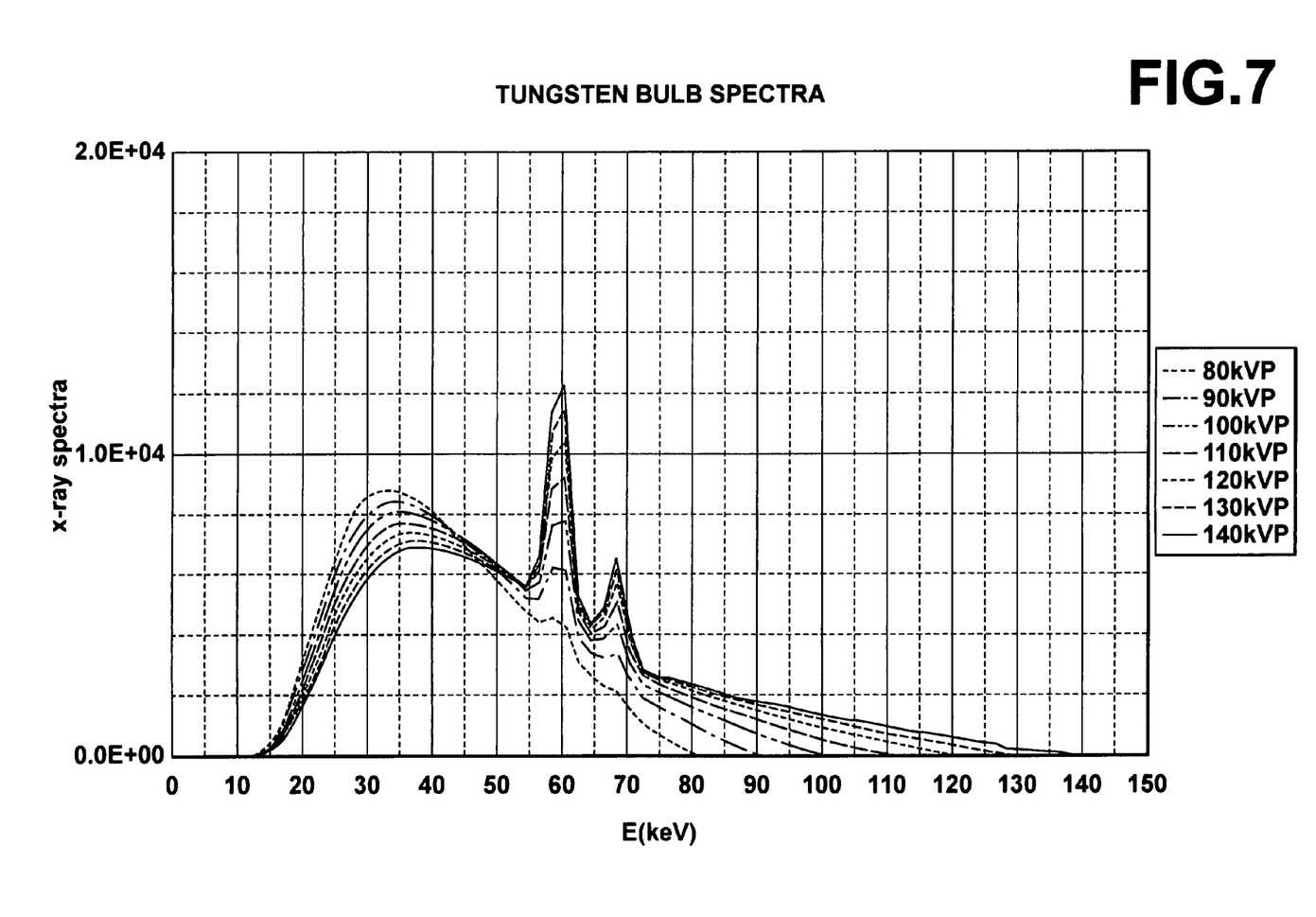
FIG. 7 is a graph that illustrates the relationship between X-ray spectra and X-ray energy at energy peaks of various X-rays.
Figure 8:
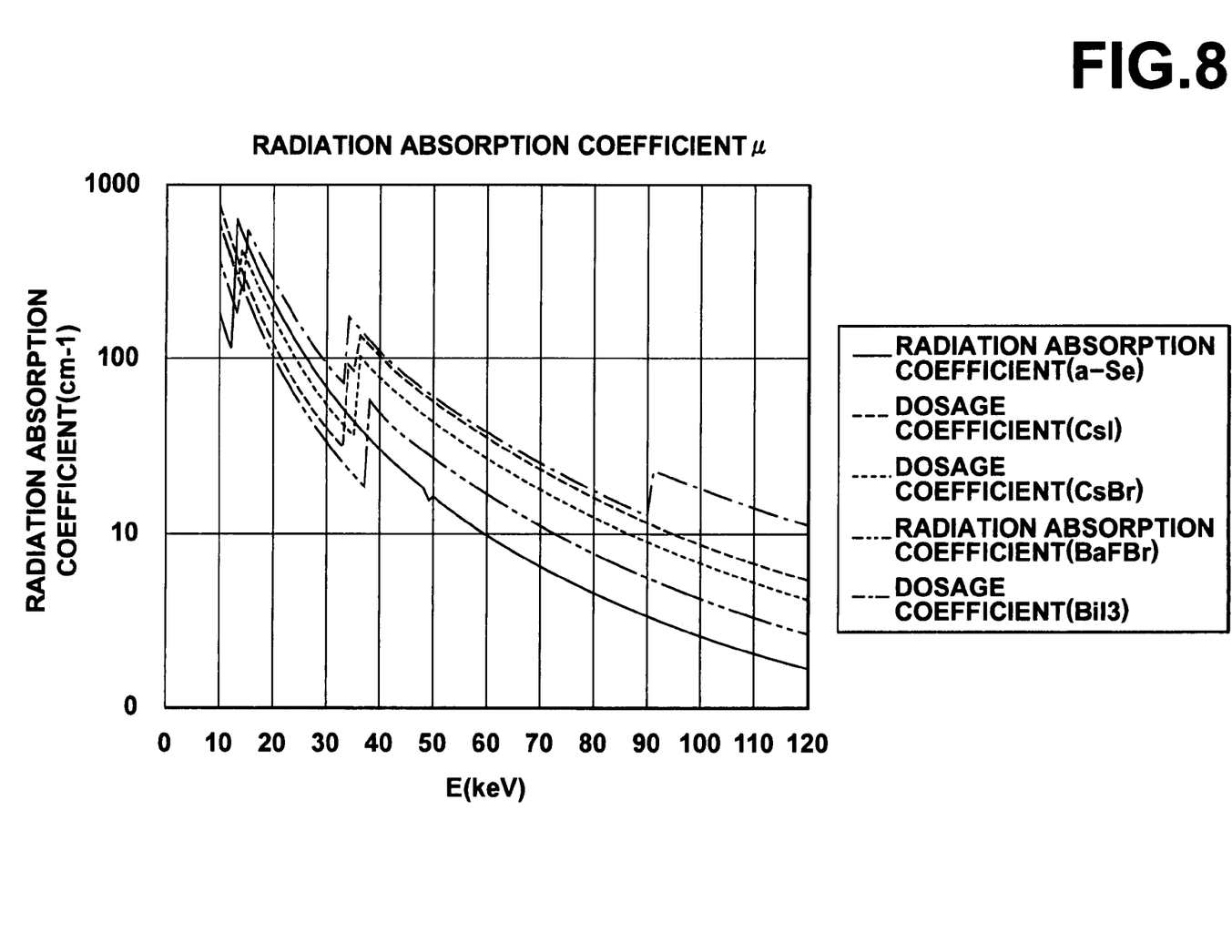
FIG. 8 is a graph that illustrates the relationship between X-ray absorption coefficients and X-ray energy for a variety of materials.

Here, a description will be given of the photoconductive layer 13 and the photoconductive layer 23, which are employed in the X-ray dosage detector 10 and the solid state detector 20, respectively. FIG. 7 is a graph that illustrates the relationship between X-ray spectra and X-ray energy at energy peaks of various X-rays. FIG. 8 is a graph that illustrates the relationship between X-ray absorption coefficients and X-ray energy for a variety of materials.

As illustrated in FIG. 7, the X-ray spectra commonly emitted from X-ray sources is not uniform at all X-ray energies. As illustrated in FIG. 8, the X-ray absorption coefficient differs for X-ray energies, depending on the material that constitutes a photoconductive layer.

For these reasons, in the case that the photoconductive layer 13 of the X-ray dosage detector 10 and the photoconductive layer 23 of the solid state detector 20 are formed by different materials, there is a possibility that the spectrum of the X-rays, which pass through the X-ray dosage detector and which are detected by the solid state detector 20, will change drastically within the X-ray dosage detector 10. If such a change in the X-ray spectrum occurs, there is a possibility that adverse influences will be imparted on the detection of X-ray images by the solid state detector 20.

Therefore, in the present embodiment, both the photoconductive layer 13 of the X-ray dosage detector 10 and the photoconductive layer 23 of the solid state detector 20 are constituted by a-Se. Thereby, adverse influences imparted on the detection of X-ray images by the solid state detector 20 are reduced, and the image quality of images detected by the solid state detector 20 is improved.

The mammography apparatus 1 comprises the control means 50, for controlling the X-ray source 2, the pressing plate moving means 60, the grid drive means 31 and the like. The film cassette 8 is equipped with a connector 35, for engaging a connector 36, which is provided on the imaging table 4. The grid drive means 31 and the comparative circuit 18 are connected to the control means 50 via the connectors 35 and 36, while the film cassette 8 is held on the imaging table 4.

Figure 6:
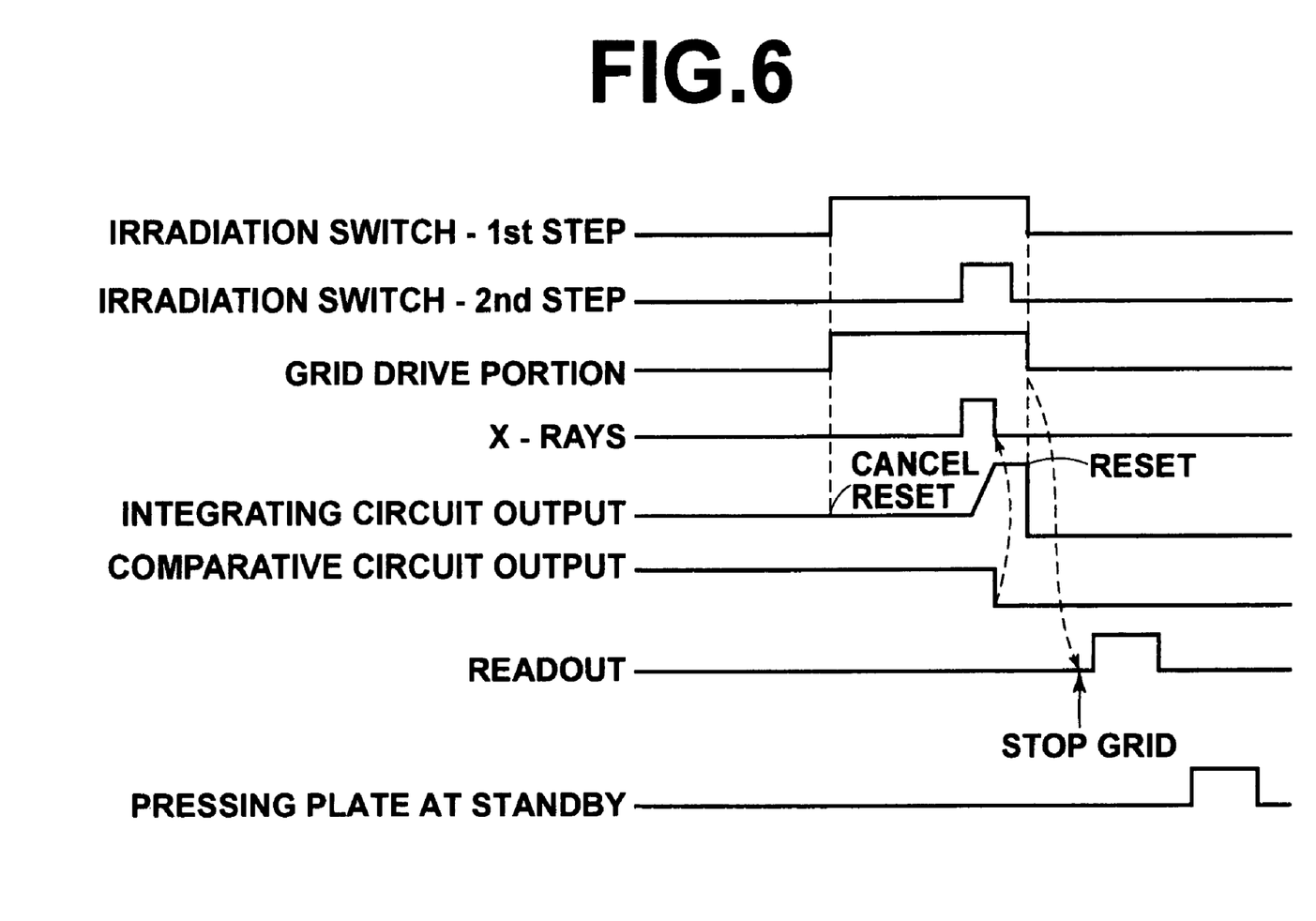
FIG. 6 is a timing chart of each operation of the mammography apparatus, from imaging to readout.

Next, the operation of the mammography apparatus 1, which is constructed as described above, will be described. FIG. 6 is a timing chart of each operation of the mammography apparatus, from imaging to readout.

During imaging, the control means drives the pressing plate moving means 60 to move the pressing plate 7 to the first position at which a breast 9 is pressed, based on commands which are manually input by an operator. Thereby, the breast 9 is fixed on the film cassette 8.

Next, the operator presses a first step of a two step irradiation switch (not shown), and the control means 50 causes the grid drive means 31 to drive the moving grid 30 and cancels resetting of the integrating circuit 17.

Thereafter, the operator presses the second step of the irradiation switch, and the control means 50 causes the X-ray source 2 to emit X-rays onto the breast 9. The X-rays, which have passed through the breast 9, that is, the X-rays that bear X-ray image information of the breast 9, are irradiated on the film cassette 8. These X-rays are detected by each of the conductive layer portions 14a of the X-ray dosage detector, and voltages corresponding to the X-ray dosage are integrated by the integrating circuit 17. Latent image charges that bear the X-ray image information are accumulated within the solid state detector. The amount of accumulated latent image charges is substantially proportional to the X-ray dosage which has passed through a subject. Therefore, the latent image charges bear the electrostatic latent image.

If the output of the integrating circuit, that is, the dosage of X-rays irradiated on the film cassette 8, exceeds a predetermined value, information indicating this fact is transmitted from the comparative circuit 18 to the control means 50, and the control means 50 stops the X-ray source when this information is received.

When the first step of the irradiation switch is released by the operator, the control means 50 causes the grid drive means 31 to stop the moving grid 30, resets the integrating circuit, and performs readout of the latent image charges from the solid state detector 20.

After readout of the latent image charges is completed, the control means drives the pressing plate moving means 60 to move the pressing plate 7 to the second position, at which the pressure on the breast 9 is released, and the process ends.

Noise becomes overlapped with the latent image charges, if vibration is imparted to the solid state detector 20 during readout of the latent image charges therefrom. However, this problem can be overcome by reading out the latent image charges from the solid state detector 20 in the manner described above.

Figure 9:
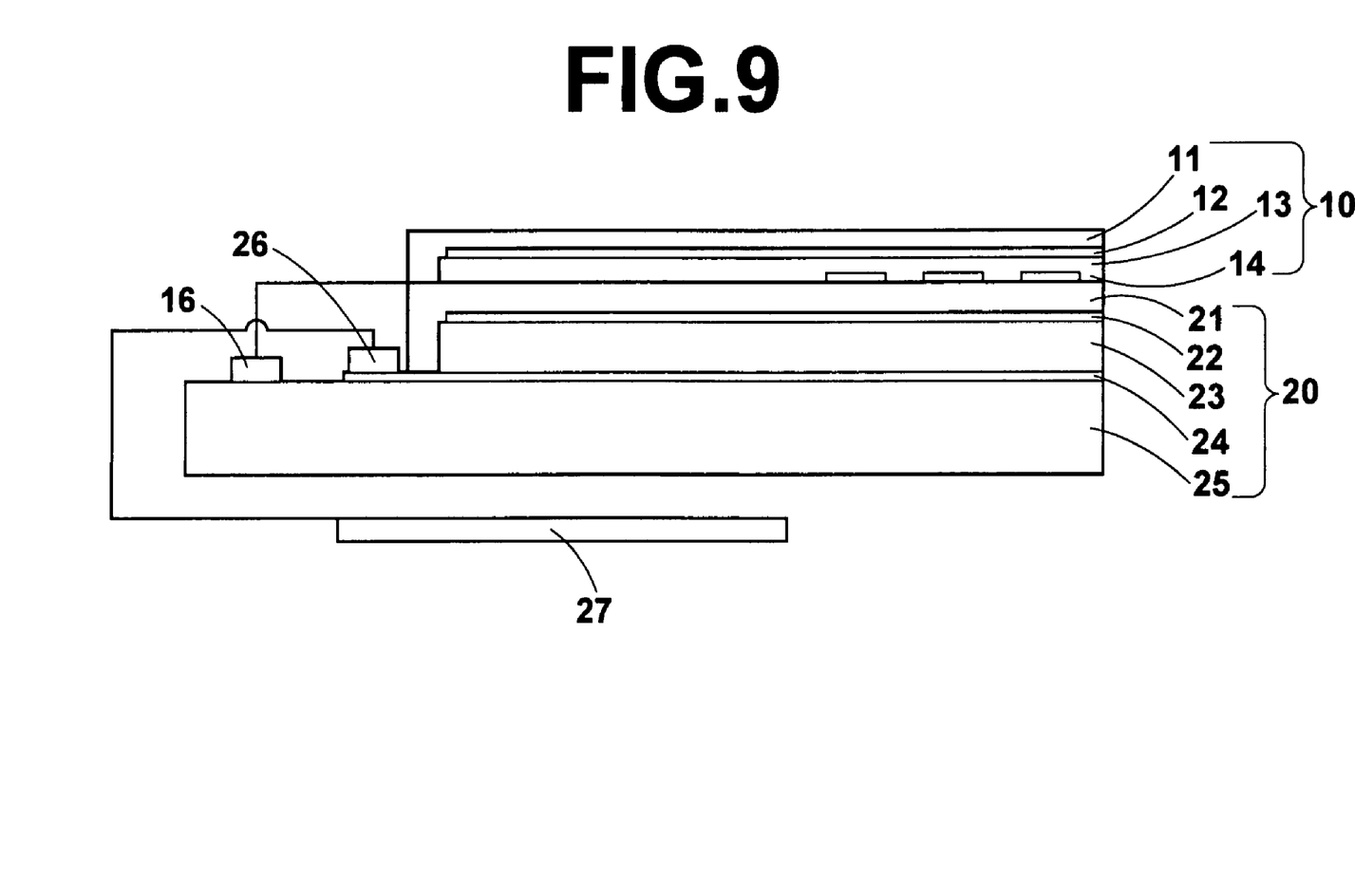
FIG. 9 is a diagram that illustrates an alternate construction of the X-ray dosage detector.

A preferred embodiment of the present invention has been described above. However, the present invention is not limited to the above embodiment. For example, the solid state detector 20 may be that of the optical readout type. In addition, the X-ray dosage detector 10 may be formed directly on the solid state detector 20 rather than on the resin substrate 15, as illustrated in FIG. 9.

What is claimed is:

1. An X-ray imaging device comprising:
a solid state detector for receiving irradiation of X-rays that bear image information to record the image information, and for outputting image signals that represent the recorded image information; and
an X-ray dosage detector, which is provided between a radiation source of the X-rays and the solid state detector, for detecting the dosage of the irradiated X-rays;
wherein the X-ray dosage detector is equipped with a photoconductive layer that exhibits photoconductivity when irradiated by X-rays, and wherein the X-ray dosage detector has conductive layers on both a front surface and a rear surface of the photoconductive layer; and at least one of the conductive layers comprises a plurality of conductive portions.

2. An X-ray imaging device as defined in claim 1, wherein:
the X-ray dosage detector is formed on a substrate, which has one of resin, carbon, and aluminum oxide as its main component.

3. An X-ray imaging device as defined in claim 1, wherein:
the solid state detector and the X-ray dosage detector are integrally formed.

4. An X-ray imaging device as defined in claim 1, wherein:
the X-ray dosage detector is capable of detecting X-ray dosages independently for a plurality of different regions of an X-ray incident surface, on which X-rays are incident.

5. An X-ray imaging device as defined in claim 2, wherein:
the X-ray dosage detector is capable of detecting X-ray dosages independently for a plurality of different regions of an X-ray incident surface, on which X-rays are incident.

6. An X-ray imaging device as defined in claim 3, wherein:
the X-ray dosage detector is capable of detecting X-ray dosages independently for a plurality of different regions of an X-ray incident surface, on which X-rays are incident.

7. An X-ray imaging device as defined in claim 1, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductive layer of the X-ray dosage detector.

8. An X-ray imaging device as defined in claim 2, wherein:
the solid state detector is equipped with a photoconductive layer that exhibits photoconductivity When irradiated by X-rays; and an X-ray absorption spectrum of the photoconductive layer of the solid state detector is substantially equal to an X-ray absorption spectrum of the photoconductive layer of the X-ray dosage detector.

9. An X-ray imaging device as defined in claim 3, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductlve layer of the X-ray dosage detector.

10. An X-ray imaging device as defined in claim 4, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductive layer of the X-ray dosage detector.

11. An X-ray imaging device as defined in claim 5, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductive layer of the X-ray dosage detector.

12. An X-ray imaging device as defined in claim 6, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductive layer of the X-ray dosage detector.

13. An X-ray imaging device as defined in claim 1, wherein:
the solid state detector is equipped with a photoconductive layer that exhibits photoconductivity when irradiated by X-rays; and an X-ray absorption spectrum of the photoconductive layer of the solid state detector is substantially equal to an X-ray absorption spectrum of the photoconductive layer of the X-ray dosage detector.

14. An X-ray imaging device as defined in claim 1, wherein:
the X-ray dosage detector and the solid state detector are housed within a casing, which is the same size as a film cassette.

15. An X-ray imaging device as defined in claim 1, wherein the photoconductive layer comprises amorphous selenium (a-Se).

16. An X-ray imaging device as defined in claim 2, wherein the photoconductive layer comprises amorphous selenium (a-Se).

17. An X-ray imaging device as defined in claim 3, wherein the photoconductive layer comprises amorphous selenium (a-Se).

* * * * *